United States Patent
Huebner et al.

(10) Patent No.: US 7,354,770 B2
(45) Date of Patent: Apr. 8, 2008

(54) SENSING DEVICE AND METHOD USING PHOTO-INDUCED CHARGE MOVEMENTS

(75) Inventors: Jay S. Huebner, Jacksonville, FL (US); Rodolfo T. Arrieta, Panama City, FL (US)

(73) Assignee: University of North Florida, Jacksonville, FL (US)

( * ) Notice: Subject to any disclaimer, the term of this patent is extended or adjusted under 35 U.S.C. 154(b) by 416 days.

(21) Appl. No.: 10/005,717

(22) Filed: Nov. 8, 2001

(65) Prior Publication Data

US 2002/0127734 A1    Sep. 12, 2002

Related U.S. Application Data

(60) Provisional application No. 60/246,880, filed on Nov. 8, 2000.

(51) Int. Cl.
*G01N 21/00* (2006.01)

(52) U.S. Cl. .................. 436/147; 436/151; 436/164; 422/82.02; 422/82.09; 422/99; 422/100; 250/338.3

(58) Field of Classification Search ............... 436/147, 436/151, 164; 422/82.02, 82.09, 99, 100; 250/338.3
See application file for complete search history.

(56) References Cited

U.S. PATENT DOCUMENTS

| | | | |
|---|---|---|---|
| 4,806,490 A | 2/1989 | Bischoff et al. | |
| 4,883,579 A | 11/1989 | Humphries et al. | |
| 4,892,640 A | 1/1990 | Wolfbeis et al. | |
| 5,074,977 A | 12/1991 | Cheung et al. | |
| 5,108,576 A * | 4/1992 | Malmros et al. | 205/777.5 |
| 5,328,847 A | 7/1994 | Case et al. | |
| 5,413,915 A | 5/1995 | Case et al. | |
| 5,468,645 A | 11/1995 | Kirollos et al. | |
| 5,500,188 A | 3/1996 | Hafeman et al. | |
| 5,567,302 A | 10/1996 | Song et al. | |
| 5,599,717 A | 2/1997 | Vo-Dinh | |
| 5,622,868 A * | 4/1997 | Clarke et al. | 436/147 |
| 5,628,890 A | 5/1997 | Carter et al. | |
| 5,679,535 A | 10/1997 | Joyce et al. | |
| 5,936,730 A | 8/1999 | Foley et al. | |
| 5,938,617 A | 8/1999 | Vo-Dinh | |
| 5,981,287 A | 11/1999 | Sinclair et al. | |
| 6,130,097 A | 10/2000 | Polzius et al. | |

* cited by examiner

*Primary Examiner*—Jill Warden
*Assistant Examiner*—Jyoti Nagpaul
(74) *Attorney, Agent, or Firm*—Thomas C. Saitta (57) ABSTRACT

A device and method which comprises a sensing surface on a membrane, solid surface or electrode, where the sensing surface contains a dye or chromophore chosen in relation to a particular target substance to be detected and quantified. The dye or chromophore is of a type which produces an electrical signal upon illumination. The particular dye or chromophore chosen for a particular target substance is one in which the presence of the target substance causes a change in the electrical signal produced. The presence of the target substance modifies the expected photo-induced charge movements (PICM) produced by the sensing surface upon illumination. The photo-induced charge movements produce signals which are detected by electronic circuits, and the presence and concentration of the target substance is determined by analyzing the difference between the PICM of the target sample versus the PICM of a control sample lacking the target substance.

4 Claims, 6 Drawing Sheets

SENSING DEVICE AND METHOD USING PHOTO-INDUCED CHARGE MOVEMENTS

This application claims the benefit of U.S. Provisional Patent Application Ser. No. 60/246,880, filed Nov. 8, 2000.

BACKGROUND OF THE INVENTION

This invention relates generally to the field of sensing devices and methods utilizing photo-induced charge movements on a surface or within a membrane or interface to indicate the presence and amount of target chemical substances such as elements, compounds or molecules, both inorganic or organic. More particularly, the invention relates to the field of devices and methods wherein particular dyes or chromophores specific to the target chemical are absorbed onto a surface or membrane and brought into contact with the target chemical analyte, wherein the dyes or chromophores generate electrical signals from charge movements upon exposure to light, and wherein the difference in photo-induced charge movements resulting from the presence of the target chemical relative to the expected photo-induced charge movements in the absence of the target chemical is analyzed to determine the presence of and the quantity of the target chemical present.

There are numerous instances where knowledge of the presence and quantity of a particular substance is required or desirable. Many qualitative and quantitative tests are known in the scientific arts. A number of these tests require either expensive equipment to analyze the test sample, analysis of the sample at a location remote from the sample collection location, or relatively long time periods to produce the result. It is an object of this invention to provide a device and a method which eliminates or reduces these drawbacks, where the detection and quantification of a target substance can be rapidly, accurately and relatively inexpensively achieved.

As an example of a target substance of negative effect in the real world, the invention can be explained using guanine as a representative target substance, guanine being the most prevalent nitrogenous waste produced by dust mites feeding on nitrogen-rich substances. It is estimated that about 5 percent of the population suffer from asthmatic or allergic symptoms attributable to house dust, with the most significant type of household allergens being contained in the feces of dust mites and in fragments of dead mite bodies, resulting from digestive enzymes excreted by the mites. Dust mite allergens are very resistive proteins, such that many common oxidizing or reducing agents, divalent and trivalent cations, alkalis, aldehydes, mild acids and some proteolytic enzymes have no effect in reducing the allergenicity of house dust mite allergens. Mite fecal pellets remain allergenic for many years, even when active mite colonies have been exterminated. Dust mite fecal pellets range from 10 to 40 microns in diameter and are easily picked up and transported by air currents. Walking, sitting, fluffing a pillow, changing bedspreads or sheets, etc. distribute the pellets into the air where they are inhaled.

Known methods for detecting the presence of dust mites through guanine include the Bischoff and Schirmacher rapid strip method, which is a qualitative method where the user compares colors of a test strip to a 4-level color chart. This method uses perishable and toxic consumables. Laboratory methods for detecting guanine quantities include High Performance Liquid Chromatography and Capillary Zone Electrophoresis, which are time consuming and relatively expensive. Other methods are used to detect specifically identified mite allergens, but currently only four such allergens are sufficiently characterized, and these four allergens belong to only two species of mites. Still other methods are used to detect the presence of the mites themselves, such as visual counts using a microscope, but the mites must be segregated from the dust samples using flotation or the like, and such processes are time consuming and relatively inaccurate. Such tests further fail to provide information on the presence or quantity of allergens, which as stated can be present in large amounts even where active colonies are not found.

Guanine is also one of the most reactive bases found in DNA and as such may prove to be a sensitive sentinel for DNA-damaging chemicals. For example, propylene oxide is a powerful DNA and guanine methylating agent which is thought to be carcinogenic, and it is estimated by OSHA that over half a million American workers are exposed to this chemical each year through direct contact with feedstock and disinfectants or by contact with residues on food surfaces.

As an example of other target substances, the invention can be used to quantify particular strains of bacteria or other microorganisms, such as for example as a means to determine if water is sufficiently sanitized for drinking purposes. Bioreactors used to produce a wide range of products from brewers yeast to human insulin can be monitored. DNA, RNA, sugars and primary amines are other target substances which may be detected.

The invention may also be used to detect and quantify metals including but not limited to Ac, Al, Ag, Am, Au, B, Ca, Cm, Co, Cr, Cu, Fe, Fl, Hf, I, In, K, Mg, Mn, Mo, Ni, Pa, Pb, Po, Pt, S, Th, Ti, U, Zn and Zr. Other target substances include but are not limited to dissolved gases, acid and alkaline phosphatases, dioxin, indole, nitrates, polysaccharides, sialomucins, skatole, sulfates, sulfomucins, trytophan, tyrosine, and uranic acid mucins.

SUMMARY OF THE INVENTION

The invention comprises a device and method of using such device which comprises a sensing surface on a membrane, solid surface or electrode, where the sensing surface contains a dye or chromophore chosen in relation to a particular target substance to be detected and quantified. The dye or chromophore is of a type which produces an electrical signal upon illumination. The particular dye or chromophore chosen for a particular target substance is one in which the presence of the target substance causes a change in the electrical signal produced. The target substance or analyte is added to a solution bathing the sensing surface to create a target sample. The presence of the target substance modifies the expected photo-induced charge movements (PICM) produced by the sensing surface upon illumination. The illumination is of short duration, and may be a single or multiple pulses of light within a chosen range of wavelengths. The photo-induced charge movements produce electrical signals which are detected by electronic circuits, and the presence and concentration of the target substance is determined by analyzing the difference between the PICM of the target sample versus the PICM of a control sample lacking the target substance.

DETAILED DESCRIPTION OF THE INVENTION

Many dyes and chromophores absorbed on interfaces of surfaces, membranes and electrodes generate transient electrical signals known as photo-induced charge movements (PICM) upon flash illumination. The surfaces or membranes may comprise any thin dielectric film, such as for example Teflon, cellulose and polyvinylalcohol, preferably less than 5 microns in thickness and most preferably less than 1 micron, as well as self-assembled monolayers (SAMs), such as formed by adsorbing alkanethiols onto gold. Other plastics, polymers and proteins may be utilized, and different materials will offer advantages for different dyes by allowing for different methods of bonding the dye to the sensing surface. In many circumstances the PICM electrical signals generated by a particular dye are modified by the presence of other chemical substances in such ways that the presence of these other substances can be detected and their amount determined by analyzing the difference in PICM between a target solution containing the target chemical substance and a control solution which does not have the target chemical solution Substances which may be detected include heavy metals, such as lead, mercury, cadmium and arsenic, some specific carbohydrates, sugars, dissolved oxygen, electrolytes, biochemicals, biomolecules, biological entities such as microorganisms, bacteria, and others. A solution's pH may also be determined. Examples of some suitable non-soluble dyes or chromophores which result in differential PICM in the presence of selected target substances are given in Table 1.

TABLE I

| Target Substance | Dye or Chromophore |
|---|---|
| calcium | PAN (1-(2-pyridylazo)-2-napthol) |
| copper | bathocuprin and dithisone |
| iron | 4,7-diphenyl-1,10-phenanthroline and benzo-{g,h,i}-perylenc-1,2-dicarboxylic acid hydrazide |
| mercury | rhodamine B, dibromofluroescein and dimethylaminobenzylidene rhodamine |
| nickel | dimethylglyoxime |
| silver | 5-(4-dimethylaminobenzylidene)-rhodamine |
| zinc | PAN (1-(2-pyridylazo)-2-napthol) |
| oxygen | chlorophyll |
| glucose | rhodamine 3B with boric acid |
| DNA, RNA | Stains-All (1-ethyl-2-{3-(1-ethylnaphtho[1,2-d]thiazolin-2-ylidene)-2-methylpropenyl}naphtho[1,2-d]thiazolium bromide) |

Figure 3:
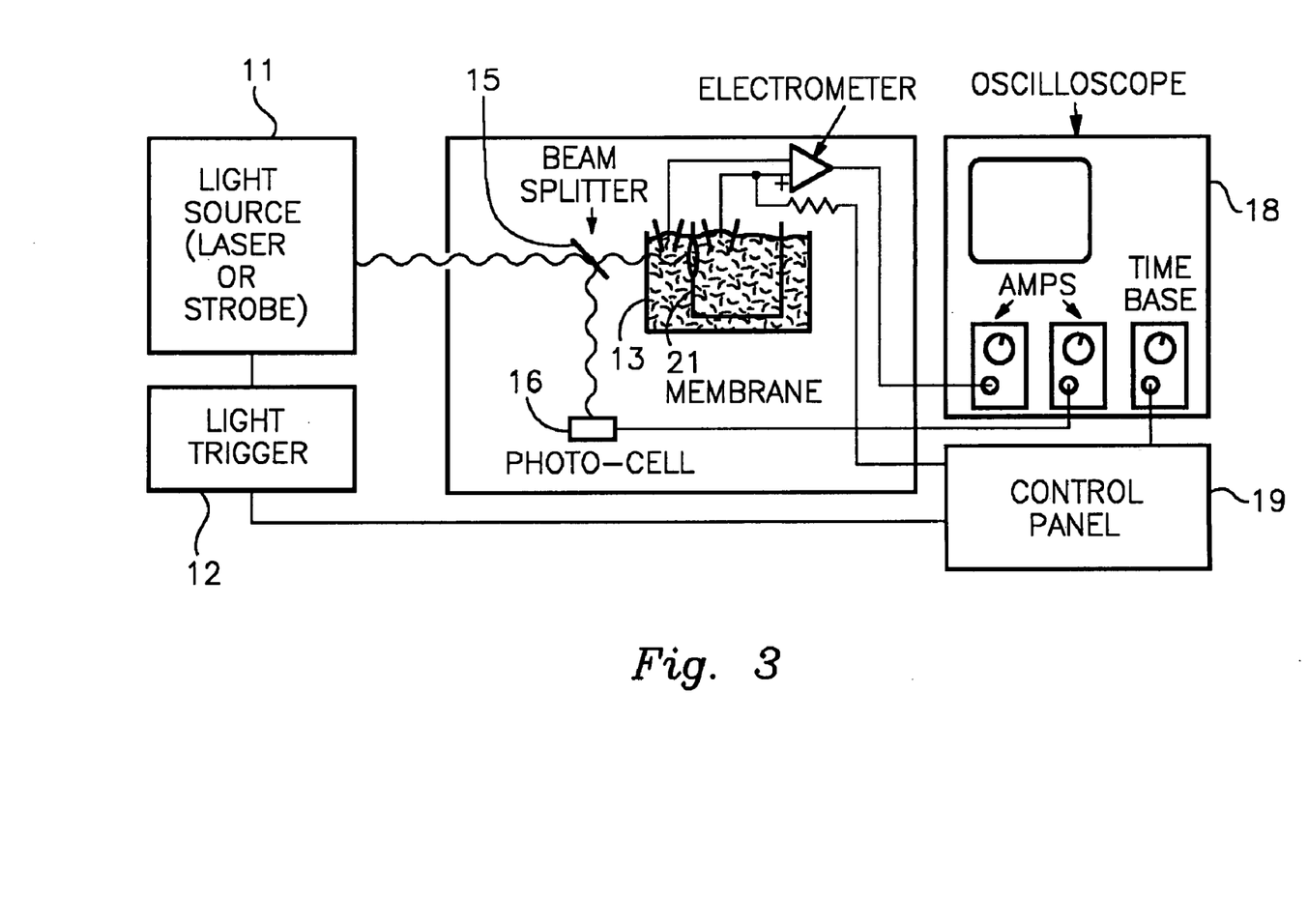
FIG. 3 is a schematic diagram of the electrometer setup.

A schematic diagram of the apparatus for the invention is shown in FIG. 3, and includes a digital oscilloscope 18 and a flash light source 11 such as a 10 ns pulsed tuneable laser, a xenon stroboscope or high intensity LEDs. The apparatus is preferably constructed using Burr-Brown OPA655 operational amplifiers with gain bandwidth product of 400 MHZ. The apparatus preferably uses RG-62/U output coaxial cables which enables the amplifier's output to settle reasonably fast. Three different oscilloscopes 18 have been used experimentally (Tektronics, Inc., Beaverton, Oreg. and Hewlett-Packard, Colorado Springs, Colo.), with the Tektronics model 468 and the HP model 54522A being able to accomplish signal averaging. Both can be operated so that a set number of noise traces can be subtracted from the same number of signal plus noise traces (obtained by blocking the light impinging on the film), thus providing significant noise reduction beyond that available from the dual electrometer. Traces used for some of the experimental work were taken from the faster HP oscilloscope 18 and digitally filtered. The light source 11 is controlled by a light trigger 12 operated by a control panel 19, and the light is directed through appropriate filters and a beam splitter 15 onto the membrane 21 and a photocell 16. Dependent on the particular dyes or chromophores, a full white spectrum or partial spectrums limited for example to UV or IR may be utilized.

Self-assembled monolayers (SAMs) used as membranes 21 incorporating dyes or pigments on solid gold or other metal electrodes 22 must be illuminated from the monolayer side and cannot normally be illuminated through the metal, though transparent and electrically conducting electrodes 22, such as tin oxide, can be used with thinly sputtered gold to hold SAMs and so could be illuminated through the electrode 22. In different arrangements, the sensing surfaces on membranes 21 can be illuminated from either side, the side with the sensing dye or the other side, with light passing through transparent membranes 21. The advantage of a transparent structure is that it would not require light to come through the test solution, which may contain materials what would reduce the light reaching the sensing surface. The dyes or chromophores may be bonded to the substrates using known mechanisms such as through hydrophobic bonds, electrostatic bonds, covalent bonds, etc. Such various techniques are well known in the textile industry for bonding dyes to fabrics of differing compositions.

A sample to be analyzed is suspended in an aqueous solution designed to dissolve the target chemical or substance. A precise aliquot of the solution is placed in a measurement container or cuvette 13 containing a measurement solution. The solution in the cuvette 13 contacts a specially prepared surface, typically a polymer film or membrane 21, having an adsorbed dye on its surface that is sensitive to the presence of the target substance. For example, in the case of guanine as the target substance, dyes from the families phenazine, rhodamine and thiazine may be used. Another similarly prepared surface is used as a blank and is not exposed to the solution containing the target substance. This control solution is used to establish a reference baseline. The target solution in the cuvette 13 is thoroughly mixed and the cuvette 13 is inserted into the charge displacement measurement apparatus. The cuvette 13 contains an internal electrode 22, which is in electrical contact with the electrometer 17 circuitry. The sensing surfaces of the membrane 21 are exposed to light with a particular spectral content for a particular duration dependent on the chosen dye or chromophore, and the dye or chromophore produces a PICM signal that is picked up by the internal electrode 22 and an external electrode 23, which is also connected to the electrometer 17. The electrodes 22 and 23 are preferably Ag/AgCl electrodes or the like provided with light shields. The PICM signal induced by the illumination of the dye is transmitted from the electrometer 17 to the oscilloscope 18 for analysis. The strength of the signal is proportional to the concentration of the target substance over the concentration range of interest when the proper dye/analyte combination is utilized.

Samples to be analyzed may include stored products, air and other gases, liquids, solids, particulates gathered on filter media or adhesive or adsorbent members, or the like. The gathering media may be worn as badges on the body or clothing, or more direct gathering by direct contact with substrates containing or retaining the target substances, such as by using a vacuum to gather particulates onto a filter, may be utilized.

Some nitrogen-containing organics or dyes/chromophores, such as aniline, carbazole, diphenylamine, guanine, 2-nitrotoluene and nirobenzene for example, may be self-detecting, in that the presence of the substance alone in the target solution will yield a change in PICM in the sensor membrane 21.

Figure 8A:
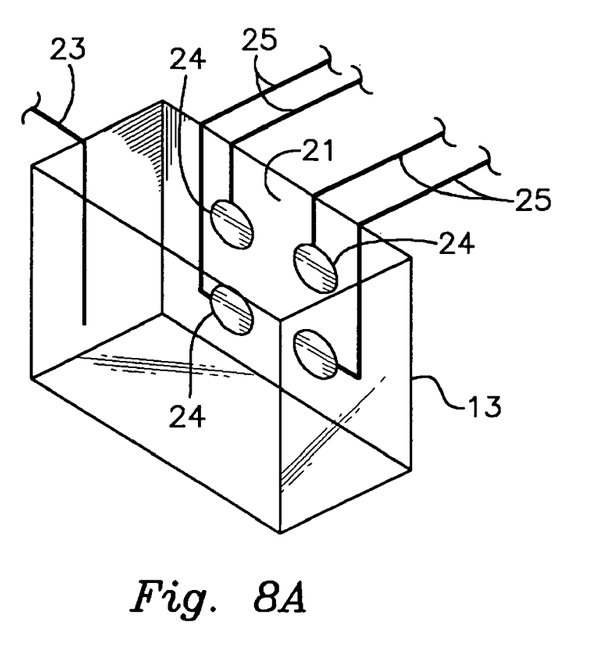
FIGS. 8a and 8b are a diagrammatic representation for a sensor with multiple sensing sites which vary in composition, along with partial circuitry required for multiple sites.
Figure 8B:
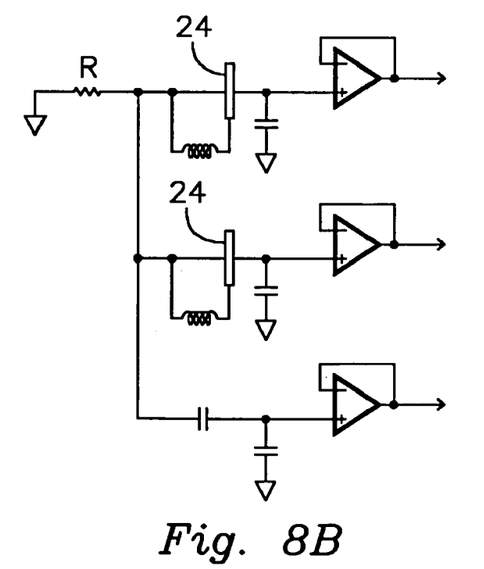

A patterned array of different dyes on a single polymer film membrane 21 or the like can be formed to produce a matrix of sensor patches 24, such as illustrated in FIGS. 8a and 8b. The matrix allows a single membrane 21 to be used to detect and quantify a plural number of target substances. The PICM waveforms would be detected by individual electrode-electrometer channels 25, the outputs of which are digitized and interpreted. The results can be read out on a digital panel in near-real time and/or downloaded to other devices.

One example of the structure and theory of the invention is a lipid bilayer membrane, which may be considered as a parallel plate capacitor in which the lipid film provides a dielectric layer between conducting aqueous solutions. Changes in the electric field distribution within the film caused by electric charge displacements within or across the film are observed as changes in the trans-membrane voltage. The time constant of light-induced molecular events, and evidence of the events themselves, which displace charge may be taken directly from film voltage vs. time recordings, provided the initial light flash is brief and the recording instruments are fast enough. Thus the film may be regarded as a transducer which along with the appropriate electronic apparatus converts PICM within the film and its vicinity into externally observable signals, which provide information about the photo-physical processes occurring in the film. PICM in thin films may also be used to study the kinetics of other molecular processes at interfaces. In principle, any light-initiated process that either displaces electric charge transversely in the film or modifies existing trans-film currents can be studied.

Figure 1A:
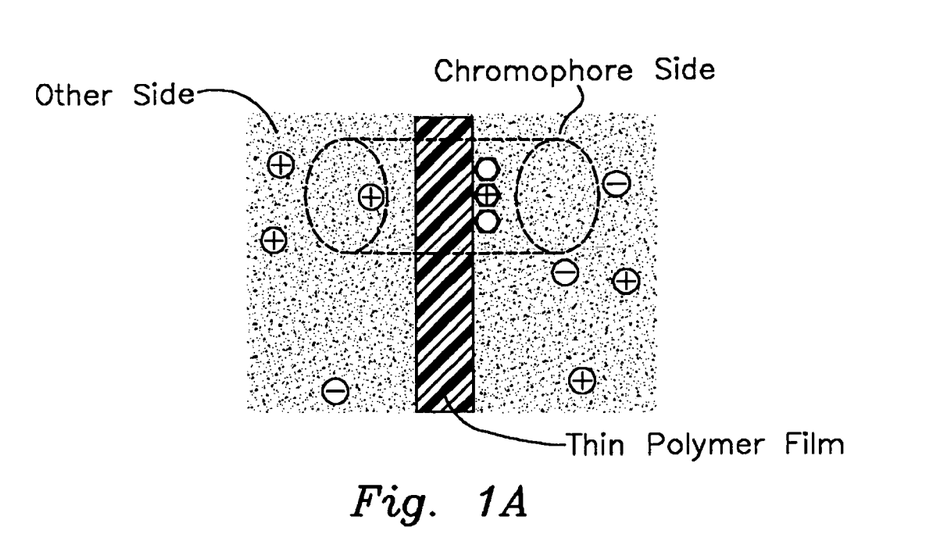
FIGS. 1a and 1b are a diagrammatic representation of a film and its surfaces, along with its equivalent electrical circuit, where the chromophoric centers are present on only one side of the film.
Figure 1B:
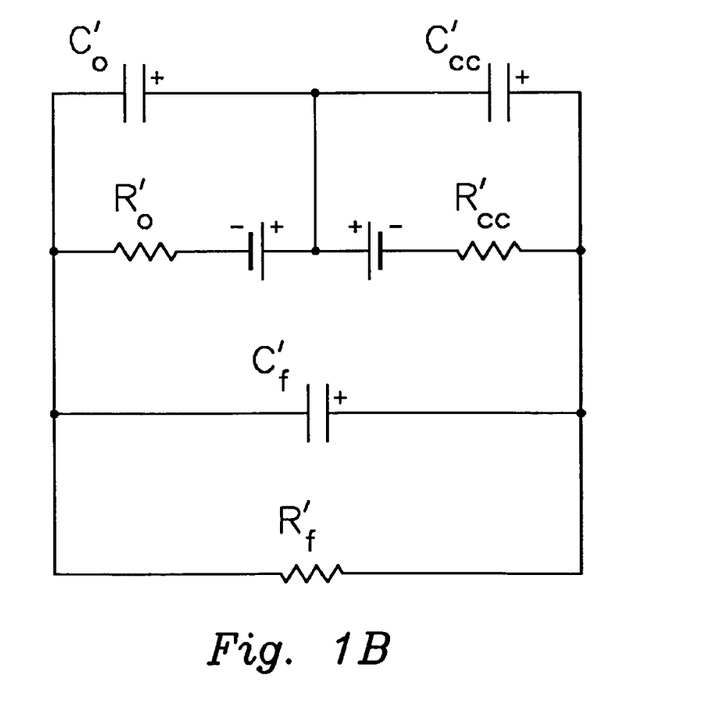

FIGS. 1a and 1b show the physical model of the chromophoric centers, which are chromophores physically or chemically embedded in the film's surface, and its equivalent electrical circuit. The film with one type of chromophoric center on one surface may be divided into n identical segments with each segment including one chromophoric center which will displace charge upon illumination. The model assumes the chromophoric center affects the film surface properties for some distance surrounding its location. In FIG. 1a, a bounding volume shown as a cylinder isolates the section of film at the site of the chromophoric center active during a particular flash and isolates this modified surface from the surrounding unaffected surface. The part of the volume on the chromophoric center's side of the film forms the circuit elements $C'_{cc}$ and $R'_{cc}$. The rest of the film within the bounding volume forms the circuit elements $C'_o$ and $R'_o$. The bounding volume is such that $C'_o$ and $C'_{cc}$ have the same cross-sectional area and their thicknesses sum to the film thickness 1. $R'_f$ and $C'_f$ are the resistance and capacitance of the unmodified region of the film's surface outside the bounding volume but still within one of the n segments that compose the sensing surface. The sensing surface's dynamic behavior will thus be the parallel combination of the dynamic behavior of the n segments.

Figure 2A:
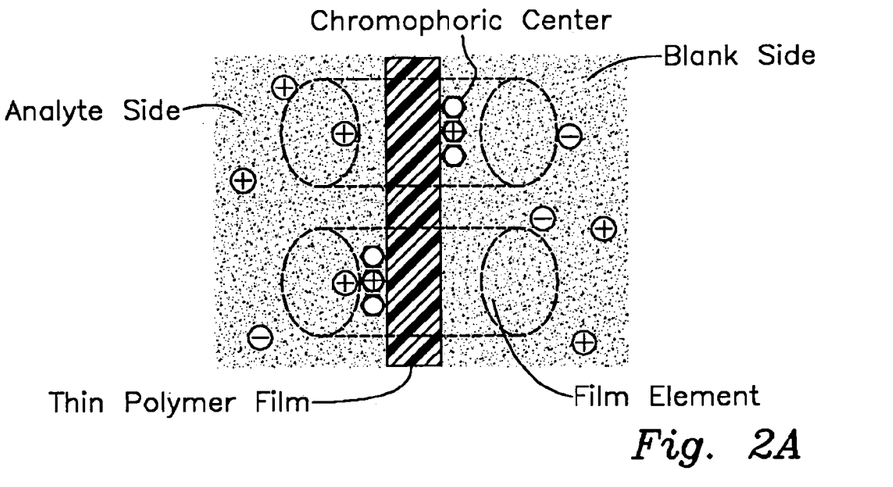
FIGS. 2a and 2b are a diagrammatic representation of a film and its surfaces, along with its equivalent electrical circuit, where the chromophoric centers are present on both sides of the film.
Figure 2B:
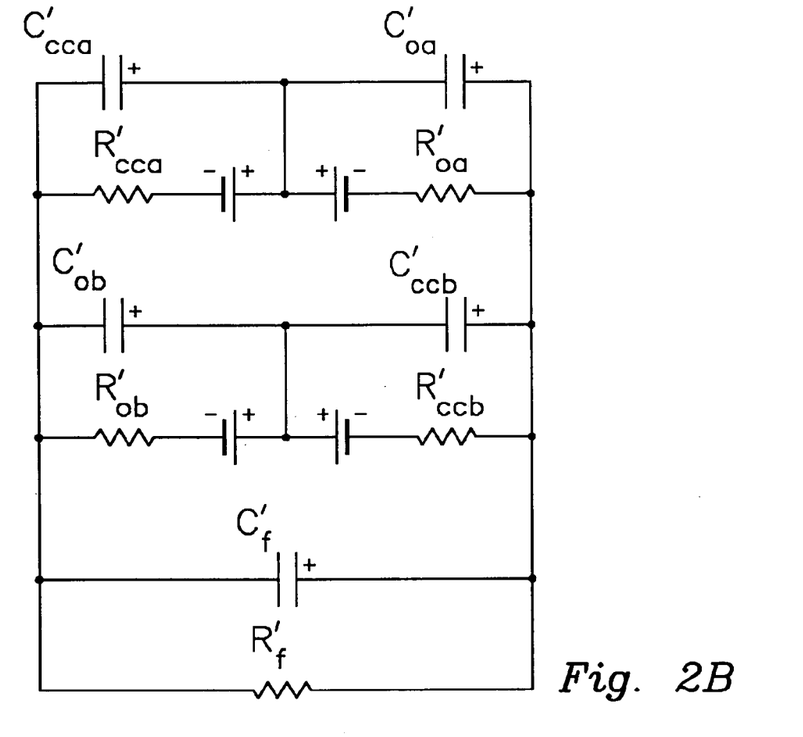

A similar model where both film surfaces contain chromophoric centers is shown in FIGS. 2a and 2b, which is a diagrammatic representation of the film and its surfaces and its equivalent electrical circuit. Here chromophoric centers are present on both sides of the film. The advantage of placing chromophoric centers on both surfaces lies in the differential nature of the signal that is obtained, such that the production of a differential signal may be used to compensate for confounding factors as long as both film surfaces are equally exposed to these factors. In the simplest sensor model, the fraction $F_a$ of chromophoric centers able or available to produce charge displacements would be the only factor affected by changes in analyte concentration. In such a simple model a center would produce an all or none response to interaction with a molecule of the analyte. Either the charge movement produced by the center will be absent until interaction with the analyte occurs, or it will be present until interaction with the analyte abolishes it.

Figure 4:
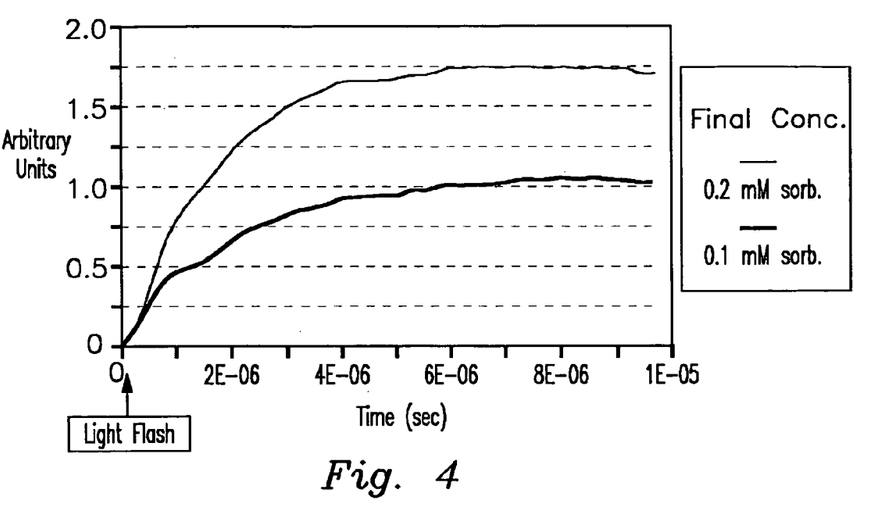
FIG. 4 is a test film reaction to sorbitol.

Films coated with a variety of chromophoric centers show sensitivity to the presence of various analytes. The most common mechanism is direct detection through complexation and either an increase or decrease of the photovoltage amplitude. FIG. 4 shows a chromophoric center interacting with hydroxyl containing molecules from the compound sorbitol. The traces show the difference between a baseline trace and a trace obtained at concentrations of 0.1 mM and 0.2 mM, with the data digitally filtered to remove noise.

Figure 5:
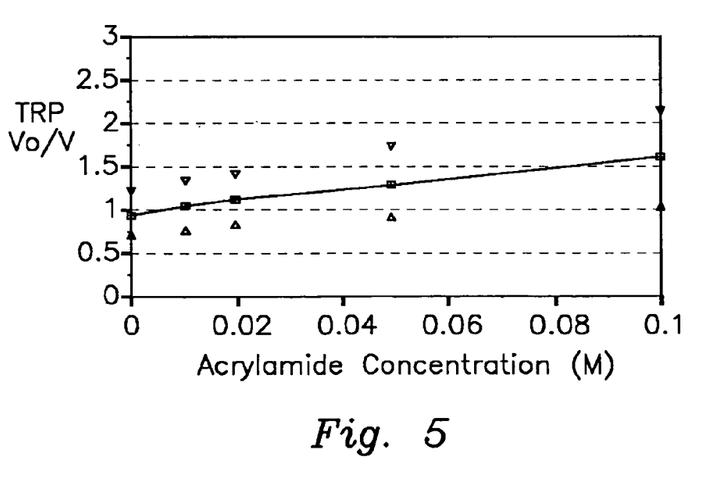
FIG. 5 is a corrected Stern-Volmer plot of acrylamide quenching of PICM mechanisms associated with excited state tryptophan.

Quenching of the electronic transitions that lead to PICM also provides a result for an effective sensor design. FIG. 5 illustrates the quenching of tryptophan PICM by acrylamide. Here linearization is achieved by assuming Stern-Volmer kinetics with a correction to remove the effects of static quenching. A variety of PICM quenchers will be assayable using this approach. For example, oxygen is known to quench the excited singlet state of many molecules.

Figure 6:
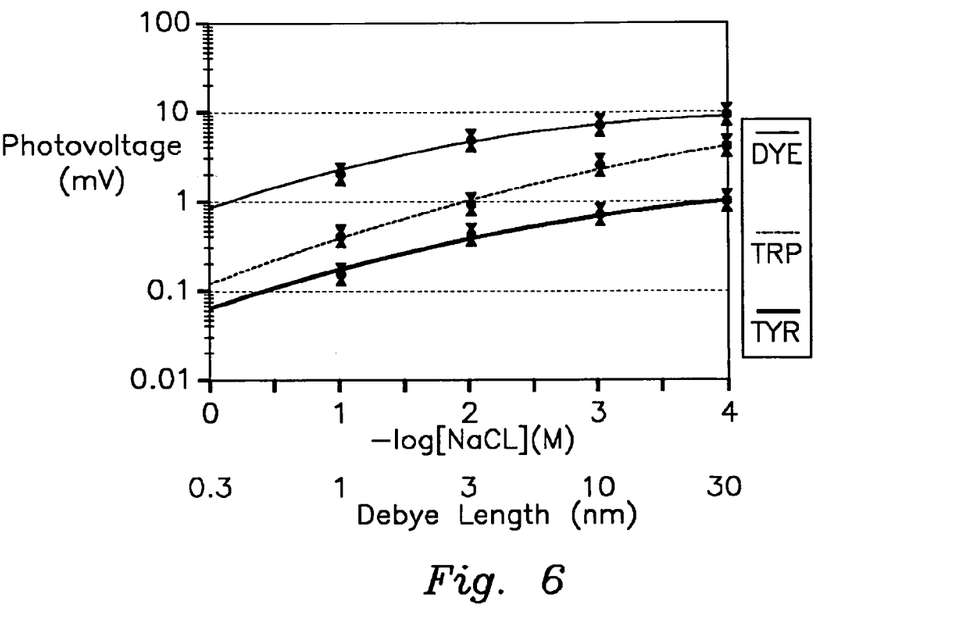
FIG. 6 is a plot of the electrolyte dependence of photovoltages of several chromophores.
Figure 7:
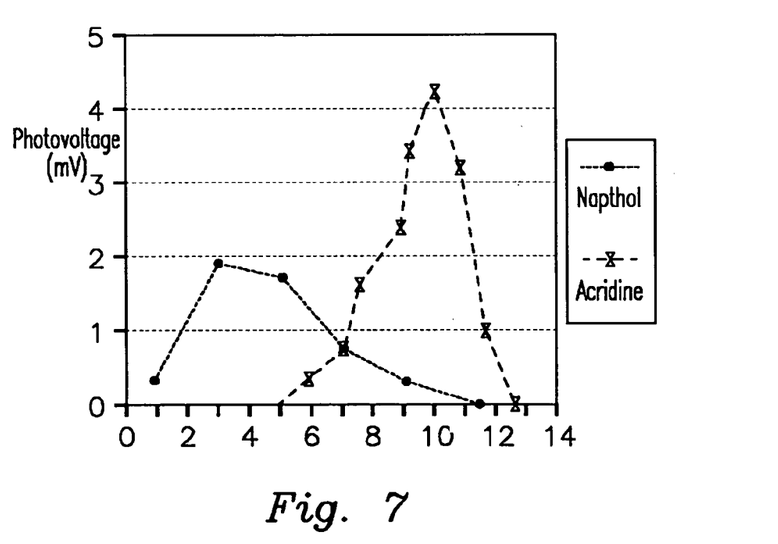
FIG. 7 is a plot of the dependence of PICM on pH for two types of chromophoric centers.

For a given sensor system, parameters such as electrolytic concentration must be determined, as this can have a profound effect on the signal amplitude. The electrolytic dependence of the chromophores Tryptophan (Trp) and Tyrosine (Tyr), both aromatic amino acids, and the carbocyanine dye diO—$C_1$-3-Cl (dye) as taken on lipid-based films are illustrated in FIG. 6. Another environmental variable that can confound a given sensor system is pH. Several chromophore families produce pH sensitive PICM, with the examples naphthol and acridine being shown in FIG. 7 and representing opposite ends of the pH scale. The lowest excited singlet state of naphthols is more acidic than the ground state, owing to electron shifts which cause aromatic alcohol deprotonation under some conditions following light absorption. At high pH this PICM is no longer possible because all the chromophores are deprotonated. On the other hand, acridine-type chromophores become a stronger base upon excitation, thus producing PICM at higher pHs. Correspondingly, the use of two such families in a sensor array allows the sensor to measure pH and apply a pH correction to any other pH sensitive chromophores in the array.

Sensor self-calibration is important in continuous sensing applications. A ratiometric procedure based on a sequence of flashes can be used to determine the parameters to be used in the electrolytic self-calibration procedure. Further, many film-chromophore combinations have been shown to have well-behaved isosbestic points which may be used to adjust for loss of active chromophore due to a variety of degradation reactions. Another approach for recalibration involves chromophoric centers that produce two distinct PICM mechanisms. When the signals generated by these mechanisms have distinct rise and fall times, they can be separated using numerical techniques such as exponential peeling. If one mechanism is sensitive to an analyte and the other is not, the signal generated by the latter can be used to calibrate the former.

Transference of the signal filtering, film condition and pH correction algorithms into a Digital Signal Processor will allow for the creation of a physical sensor device based on a miniature flash lamp, analog-to-digital converter, DSP engine and sensor array, similar in size and ease of use to a disposable film camera.

Examples of successful dye/target substance combinations which produce PICM which can be sufficiently analyzed to produce evidence as to the presence of the target substance and typically its concentration follow.

EXAMPLE 1

The dye 4,7-diphenyl-1,10-phenanthroline was adsorbed on a membrane. A strobe flash produced a positive signal of 2.6 mV at 20 microseconds after the strobe flash. This produced the control baseline. In the presence of 2.5 mM ferric (iron III) ions, the signal at 20 G microseconds was 5.0 mV negative, showing that the presence of iron ions can be detected through the change in PICM. Subsequent experimentation at lower iron concentrations indicate that 5 nanomolar changes in concentration are distinguishable.

EXAMPLE 2

Dimethylglyoxime absorbed on a Teflon membrane to produce a sensing layer a few monolayers thick when evenly distributed as a control produces a positive photovoltage from UV strobe illumination, with a peak amplitude of negative 0.4 mV occurring in about 1.0 millisecond. This signal is incrementally reduced by incremental additions of nickel chloride to the target solution, to the point that no photovoltage is observed for 100 micromolar or higher concentrations.

EXAMPLE 3

A membrane was prepared with the dye Stains-All, a cationic carbocyanine dye, and a baseline from a control target sample was obtained. DNA was provided at a concentration of 0.1 microgram per ml in a target sample, and the PICM signal was reduced at 0.5 milliseconds from positive 48 mV to less than positive 0.1 mV. Further experimentation showed that incremental additions of DNA in the target solution resulted in corresponding incremental reductions in the photovoltage results.

EXAMPLE 4

A membrane was prepared with the dye Stains-All, a cationic carbocyanine dye, and a baseline from a control target sample was obtained. RNA was provided at a concentration of 0.1 microgram per ml in a target sample, and the PICM signal was reduced at 50 microseconds from positive 10 mV to negative 10 mV.

EXAMPLE 5

The detection of microorganisms such as bacteria is based on the polysaccharide fraction of bacterial lipopolysaccharides (LPS). This fraction is easily cleaved from the surface of bacterial cells through a variety of treatments, and comprises an O-antigen fraction which serologically defines a particular strain of bacteria and a core polysaccharide fraction which varies little among strains of a particular bacteria species. The core polysaccharides of the vast majority of Gram-negative bacteria start with a disaccharide of 3-deoxy-D-manno-octulosonic acid. This sugar (known as KDO) is almost exclusively found as part of LPS. The invention uses a sensitive polysaccharide sensor using KDO and its oligosaccharides. Crosslinked lipid monolayers supported on either side of an ultrathin plastic membrane are used as the substrate for signal transduction. The membrane's surfaces are covered with chemically selective sites and chromophoric centers that are sensitive to the occupation of the selective sites. The geometry allows nearly equivalent light energy to interact with both sides of the membrane, thus canceling out all variations except those caused by changes in the analyte concentration on the outside solution. The membrane is a differential sensor with the chemically unexposed side serving as the blank or control.

The sensing surface consists of a layered membrane structure that has been modified with two types of custom-designed molecules in special arrangements. One molecule is a monomer containing a reversible hydroxyl binding group, and the other is a reporting chromophore. Both of these molecules are anchored to the membrane. Selective sites on the membrane are created with the reporter chromophores embedded therein. The assemblages are stabilized by chemical, electrochemical and/or photochemical crosslinking to fix the geometry of the selective sites, a process known as imprinting. The imprinting fixes the reactive groups in the right configuration to specifically recognize the analyte. Both the binding group molecules and chromophoric molecules also possess functional groups that allow them to bind to each other and to the membrane's lipid layers. To make the sensor selective to an analyte the sensor is exposed to the analyte and the membrane is crosslinked, which fixes the reactive groups in the right configuration to recognize the analyte. The sensor is then washed to remove the template.

The electrometer uses three mini-DIP OPA655 operational amplifiers in a design which cancels most of the radio frequency noise induced in proximate pulsed light sources by using a pair of electrodes, one sensing the PICM induced signals and the other monitoring a cell of comparable geometry but with no chromophores. The design is implemented in surface mount technology to achieve multiple channels of the required density to implement the membrane sensor matrix. Stroboscopes may be utilized to produce the light flash illuminations. Filters may be utilized to modify the composition of illuminating spectra incident on individual membrane sections.

EXAMPLE 6

Another mechanism for inducing PICM is photoinduced redox reactions. For example, experiments have been carried out using chlorophyll and NaI as a sensitive indicator of dissolved oxygen. In these experiments the photovoltage decreases to 10% of its amplitude in air when the solution contacting the sensing surface is purged with nitrogen. The mechanism involves oxidation of the iodide anion by photo-excited chlorophyll and oxidation of the reduced ground state chlorophyll by oxygen. The net effect of these reactions is the production of large, lipophilic polyiodide anions that can permeate many types of nonpolar films. The signal is quite large if the film is highly permeable to the polyiodide ions that are formed. An imposed transfilm voltage leads to observable photoinduced transfilm conductance changes which are proportional to the number of polyiodide ions permeating the film.

Photoinduced redox reactions that do not lead to transfilm conductance changes can also be detected through PICM, provided that charged species are produced which undergo a net charge displacement transverse to the film-solution interface. Examples include amino acids, porphyrins, synthetic dyes, fullerenes and transition metal complexes such as bipyridine ruthenium II and ferricyanide.

The methodology of the invention can be summarized as follows:

A method for detecting the presence of a target substance in a solution comprising the steps of:
  providing a sensing device to sense the photo-induced charge movements resulting from illumination of a dye which is in contact with said target substance;
  choosing a dye which produces photo-induced charge movements upon illumination and which produces a different amount of photo-induced charge movements upon illumination when in contact with said target substance;
  adsorbing said dye onto a membrane;
  illuminating said dye;
  detecting and analyzing the photo-induced charge movements resulting from illumination of said dye when not in contact with said target substance to provide a baseline value;
  placing said target substance in solution in contact with said dye;
  illuminating said dye;
  detecting and analyzing the photo-induced charge movements resulting from illumination of said dye when in contact with said target substance;
  comparing the baseline value results from illumination of said dye when not in contact with said target substance to the results obtained from illumination of said dye when in contact with said target substance to determine if said target substance is present;
  successively detecting and analyzing the photo-induced charge movements resulting from illumination of said dye when in contact with different concentrations of said target substance to produce comparative concentration values;
  comparing the results from illumination of said dye when in contact with said target substance to the comparative concentration value results obtained from illumination of said dye when in contact with different concentrations of said target substance to determine the concentration of said target substance;
  wherein said illumination step is performed with a duration of milliseconds or less;
  wherein said illumination step is performed over a chosen wavelength range;
  and further wherein:
  wherein said dye is a first dye and said target substance is a first target substance, further comprising the steps of:
    successively detecting and analyzing the photo-induced charge movements resulting from illumination of said first dye when in contact with different concentrations of said first target substance to produce comparative concentration values;
    comparing the results from illumination of said first dye when in contact with said first target substance to the comparative concentration value results obtained from illumination of said first dye when in contact with different concentrations of said first target substance to determine the concentration of said first target substance
    providing at least one different dye from said first dye and adsorbing said at least one different dye onto said membrane, wherein said at least one different dye produces photo-induced charge movements upon illumination and which produces a different amount of photo-induced charge movements upon illumination when in contact with a different target substance;
    placing said different target substance in contact with said at least one different dye simultaneously with placing said first target substance in contact with said first dye;
    illuminating said at least one different dye simultaneously with illuminating said first dye;
    detecting and analyzing said photo-induced charge movements from said at least one different dye;
    successively detecting and analyzing the photo-induced charge movements resulting from illumination of said at least one different dye when in contact with different concentrations of said different target substance to produce comparative concentration values;
    comparing the results from illumination of said at least one different dye when in contact with said different target substance to the comparative concentration value results obtained from illumination of said at lest one different dye when in contact with different concentrations of said different target substance to determine the concentration of said different target substance.

It is understood that equivalents and substitutions for certain components and steps set forth above may be obvious to those skilled in the art, and therefore the true scope and definition of the invention is to be as set forth in the following claims.

We claim:

1. An apparatus for detecting the presence and concentration of a target substance in a solution through differences in photo-induced charge movements between a control solution and a target solution containing the target substance, wherein a dye is utilized which produces photo-induced charge movements upon illumination and which produces a different amount of photo-induced charge movements upon illumination when in contact with said target substance, the apparatus comprising:
  a light source for illumination;
  a container to receive a target solution containing a target substance;
  a membrane disposed within said container;
  a dye adsorbed onto said membrane which produces photo-induced charge movements upon illumination and which produces a different amount of photo-induced charge movements upon illumination when in contact with said target substance, said dye being in contact with said target solution;
  an electrometer in electrical communication with said membrane to detect said photoinduced charge movements relative to said membrane and to generate a signal for analysis;
  means to analyze said signal to determine the presence and concentration of said target substance.

2. The apparatus of claim 1, wherein said light source is chosen from the group of light sources consisting of lasers, stroboscopes and LEDs.

3. The apparatus of claim 1, wherein said membrane is self-assembled monolayer.

4. The apparatus of claim 1, where said analyzer means is an oscilloscope.

* * * * *